United States Patent [19]
Fitzgerald et al.

[11] Patent Number: 5,338,543
[45] Date of Patent: Aug. 16, 1994

[54] THIMEROSAL INACTIVATED MYCOPLASMA HYOPNEUMONIAE VACCINE

[75] Inventors: Gerald R. Fitzgerald, Earlham; C. Joseph Welter, Des Moines, both of Iowa

[73] Assignee: Ambico, Inc., Dallas Center, Iowa

[21] Appl. No.: 889,911

[22] Filed: May 29, 1992

Related U.S. Application Data

[63] Continuation-in-part of Ser. No. 841,632, Feb. 27, 1992, abandoned.

[51] Int. Cl.$^5$ .............................................. A61K 39/02
[52] U.S. Cl. ............................... 424/264.1; 435/252.1; 435/870; 424/825
[58] Field of Search ................... 424/92, 252.1, 870

[56] References Cited

U.S. PATENT DOCUMENTS

| | | | |
|---|---|---|---|
| 2,908,614 | 10/1959 | Muggleton et al. | 424/92 |
| 3,522,790 | 10/1970 | Greegberg et al. | 116/215 |
| 3,632,741 | 1/1972 | Wittmann et al. | 424/89 |
| 3,917,819 | 11/1975 | Yoshioka et al. | 424/88 |
| 4,058,599 | 11/1977 | Bauer | 424/92 |
| 4,855,227 | 8/1989 | McGarrity | 435/7.32 |
| 4,894,332 | 11/1990 | Schaller et al. | 435/69.3 |
| 4,985,243 | 1/1991 | Faulds et al. | 424/85.8 |
| 5,004,607 | 4/1991 | Ragland et al. | 424/88 |
| 5,064,647 | 11/1991 | Storm | 424/92 |

FOREIGN PATENT DOCUMENTS

| | | |
|---|---|---|
| 0196215 | 10/1986 | European Pat. Off. . |
| 0283840 | 9/1988 | European Pat. Off. . |
| 0325191 | 7/1989 | European Pat. Off. . |
| 0345021 | 12/1989 | European Pat. Off. . |
| 0359919 | 6/1990 | European Pat. Off. . |
| 0475185 | 3/1992 | European Pat. Off. . |
| 1924304 | 12/1970 | Fed. Rep. of Germany . |
| 75100 | 9/1980 | Romania . |
| 8600019 | 1/1986 | World Int. Prop. O. . |
| 8800977 | 2/1988 | World Int. Prop. O. . |
| 9111717 | 8/1991 | World Int. Prop. O. . |
| 9118627 | 12/1991 | World Int. Prop. O. . |
| 9203157 | 3/1992 | World Int. Prop. O. . |

OTHER PUBLICATIONS

Chen, K. S. et al., "Adjuvant Enhancement of Humoral Immune Response to Chemically Inactivated Bovine Viral Diarrhea Virus", *Canadian Journal of Comparative Medicine*, 49:91–94 (Jan. 1985).

Gupta, R et al., "Effects of Elevated Temperatures on the Opacity and Toxicity of Pertussis Vaccines Manufactured with Different Inactivating Agents", *Biological Abstracts* 82(11): 102519 1986.

Mirchamsy, H. A. et al., "Active Immunization of Cattle with Killed Vaccines Prepared from Cell–Cultural Rinderpest Virus", *Biological Abstracts* 62(8):43171 1976.

Petersen et al, *Proc. Amer. Assoc. Swine Pract.*, Mar. 1991, pp. 17–21.

Wise et al., *Journal of Bacteriology*, 169: 5546–5555 (1987).

Dayalu, Proceedings: Mycoplasma Pneumonia Symposium, Smith Kline Beecham, 1–15 (1990).

Kishima et al, *Veterinary Microbiology*, 13: 335–42 (1987).

*Primary Examiner*—Marian Knode
*Attorney, Agent, or Firm*—Iver P. Cooper

[57] ABSTRACT

The invention relates to a method for making an inactivated vaccine of *Mycoplasma hyopneumoniae* by inactivating the bacteria with Thimerosal. The resulting bacterin is mixed with an adjuvant of aluminum hydroxide and DEAE dextran and injected into pigs. The resulting bacterin and adjuvant mixture can also be mixed with other bacteria such as Borderella and Pasteurella, for further adjuvant effect. Protective immunity against mycoplasmal pneumonia is elicited in swine using these vaccines.

12 Claims, No Drawings

THIMEROSAL INACTIVATED MYCOPLASMA HYOPNEUMONIAE VACCINE

This application is a continuation-in-part of Ser. No. 07/841,632, filed Feb. 27, 1992, hereby incorporated by reference and now abandoned.

FIELD OF THE INVENTION

The present invention relates to methods for preparing *Mycoplasma hyopneumoniae* vaccines and diagnostic agents.

BACKGROUND TO THE INVENTION

Chronic pneumonia in swine has been recognized as a major problem in swine production for almost a century. The disease has a high morbidity with low mortality causing a chronic cough, dull hair coat, retarded growth and unthrifty appearance lasting several weeks. Characteristic lesions of purple to gray areas of consolidation particularly in ventral apical and cardiac lobes are observed in infected animals. Death may result from secondary infection or stress. One of the causes of chronic pneumonia is infection by *Mycoplasma hyopneumoniae*. Economic losses alone have been estimated at between 200 to 250 million dollars annually.

The bacteria was first identified in 1965. *Mycoplasma hyopneumoniae* is a slow growing, fastidious bacterium which lacks a cell wall. It is frequently difficult to isolate from the respiratory tract due to *Mycoplasma hyorhinis*, a common secondary agent also located in the respiratory tract.

The disease is spread by aerosol, produced by coughing, and by direct contact from an affected or convalescent carrier swine. Mingling of infected animals and uninfected animals results in early and frequent reinfection. Infection frequently starts with infection of piglets by carrier sows at farrowing. Because of current herd management techniques, infection may remain silent until later in life. Additional infection usually is observed after weaning when pigs are pooled. Overt disease is normally observed in pigs at six weeks of age or older. Average animal growth rates are reduced by about 16% with feed conversion rates being reduced by about Surveys of slaughtered animals revealed lesions typical of *Mycoplasma pneumonia* in 30–80% of swine. Results from 337 herds in 13 states indicated that 99% of the herds had hogs with pneumonia lesions typical of *Mycoplasma pneumonia*. Therefore, the need for effective preventative and treatment measures are great.

Tiamulin, trimethoprim, tetracyclines and lincomycin have been shown to have some benefit. However, antibiotics are expensive and require prolonged use. Additionally, reinfection is an ever present problem. Antibiotics have not been shown to effectively eliminate spread of *Mycoplasma hyopneumoniae*. Prevention by maintaining pathogen free herds is possible but reintroduction of *Mycoplasma hyopneumoniae* occurs.

Vaccines generally employ one of four categories of antigens: live microorganisms administered via an unnatural route, live attenuated microorganisms, killed microorganisms and fractions or even a single antigen or product of a microorganism. In all situations, the goal is to present antigens without giving the disease. A number of different inactivating agents and means have been employed including formalin, azide, freeze-thaw, sonication, heat treatment, sudden pressure drop, detergent (especially non-ionic detergents), lysozyme, phenol, proteolytic enzymes and propiolactone.

Thimerosal has been proposed for inactivation of certain bacteria unrelated to Mycoplasma in Greenberg et al. U.S. Pat. No. 3,522,790 and Muggleton et al, U.S. Pat. No. 2,908,614. Ragland et al. U.S. Pat. No. 5,004,607 inactivates their bacteria with formalin (column 4, line 59) but also later adds Thimerosal as a preservative. Thimerosal has not previously been used to inactivate *Mycoplasma hyopneumoniae* for vaccine use.

RespiSure vaccine sold by Smith Kline Beecham is a chemically inactivated *Mycoplasma hyopneumoniae* vaccine administered with an oil adjuvant. Petersen et al. *Proc. Amer. Assoc. Swine Pract.*, March 1991, p. 17–21 discloses inactivating *Mycoplasma hyopneumoniae* with formalin to produce a bacterin for potential vaccine use. Faulds et al., U.S. Pat. No. 4,985,243 uses freeze-thaw to extract antigens from *Mycoplasma hyopneumoniae* in order to prepare a vaccine.

Recombinant DNA techniques have been used to express an antigen which had potential for use as a vaccine. Schaller et al. U.S. Pat. No. 4,894,332.

*Mycoplasma hyopneumoniae* has been lysed and analyzed in terms of its proteins, for example, Wise et al. *Journal of Bacteriology*, 169: 5546–5555 (1987). However, it has not been established which one or ones are the critical proteins which must be recognized to elicit a protective immune response.

A number of vaccines in the past have used adjuvants to enhance the immunogenicity of an antigen. The mechanism of how adjuvants operate is not entirely known. Some are believed to enhance the immune response by slowly releasing the antigen while other adjuvants are strongly immunogenic in their own right and are believed to function synergistically. Among the adjuvants which have been used in various vaccines include, oil and water emulsions, complete Freund's adjuvant, incomplete Freund's adjuvant, *Corynebacterium parrum*, Hemophilus, *Mycobacterium butyricum*, aluminum hydroxide, dextran sulfate, iron oxide, sodium alginate, Bacto-Adjuvant, certain synthetic polymers such as poly amino acids and co-polymers of amino acids, saponin, iota carrageenan, Regressin TM, Avridine TM, Mannite monooleate, paraffin oil, and muramyl dipeptide.

Yoshioka et al., U.S. Pat. No. 3,917,819, used an aluminum hydroxide gel as an adjuvant in a formalin-killed *Mycoplasma suipneumoniae* vaccine, while Dayalu, Proceedings: *Mycoplasma pneumonia* Symposium, Smith Kline Beecham, 1–15 (1990) states on page 12 that Kobisch et al (1987) used aluminum hydroxide in a *Mycoplasma hyopneumoniae* vaccine. Kishima et al., *Veterinary Microbiology*, 13: 335–42 (1987) have used dextran sulfate as an adjuvant in an azide-killed mycoplasma vaccine. Outside the field of bacterial vaccines, Roumanian Patent 75,100 has proposed a viral vaccine using aluminum hydroxide and DEAE dextran as an adjuvant. However, this combination has not been used to our knowledge with any bacteria, let alone as an adjuvant with Mycoplasma.

Regardless, the goal of a vaccine is to provide protection against natural infection. A detectable immune response, such as producing detectable quantities of antibodies, may not necessarily be protective. Thus, while vaccines have been attempted to protect swine from infection by *Mycoplasma hyopneumoniae*, acceptable levels of protection have not been achieved.

SUMMARY OF THE INVENTION

It is an object of the invention to provide a method for preparing a *Mycoplasma hyopneumoniae* bacterin which elicits a protective immune response when administered in a vaccine.

It is another object of the invention to provide a method for inactivating *Mycoplasma hyopneumoniae*, in a manner which preserves its antigenicity and its ability to elicit a protective immune response.

It is another object of the invention to provide a vaccine for *Mycoplasma hyopneumoniae* which does not interfere with and is not interfered by another bacterial vaccine.

It is another object of the invention to provide a synergistic combination vaccine.

It is another object of the invention to provide an adjuvant which will adequately present a bacterial antigen, particularly a *Mycoplasma hyopneumoniae* bacterin in a vaccine.

It is another object of the invention to provide antigens which are specifically recognized by antibodies produced by animals infected or previously infected with *Mycoplasma hyopneumoniae* effective for an immunoassay.

It is another object of the invention to provide a test for whether or not cultivated *Mycoplasma hyopneumoniae is virulent.*

It is another object of the invention to prepare a bacterial adjuvant of aluminum hydroxide and DEAE Dextran which helps elicit an effective protective response in immunized animals.

In contrast to the previous attempts to prepare an effective vaccine against *Mycoplasma hyopneumoniae*, in a preferred embodiment, the present invention employs a low passage *Mycoplasma hyopneumoniae* inactivated with Thimerosal (sodium ethyl mercury thiosalicylate) and an adjuvant of aluminum hydroxide and DEAE Dextran in combination to prepare an effective vaccine. This vaccine provides protection to pigs injected with it against mycoplasmal pneumonia. Combinations of this vaccine with other vaccines conventionally given to swine may also be used.

DESCRIPTION OF THE PREFERRED EMBODIMENTS

For the preparation of a vaccine protective against infection from *Mycoplasma hyopneumoniae*, the present invention employs inactivated bacteria. Many microorganisms lose their infectivity and change antigens when grown in culture for many generations. Indeed, the standard vaccine for polio is essentially a live polio virus which after growing in culture for many generations has mutated so that it no longer grows in nerve or brain tissue and thus has lost much of much of its pathogenicity. For this virus, the critical antigens have not changed.

Suitable strains of *Mycoplasma hyopneumoniae* may be obtained from a variety of sources. One obvious source is from the authors of any of the above listed publications involving *Mycoplasma hyopneumoniae*. Strains may also be obtained from depositories such as the ATCC and NRRL. The ATCC alone lists six strains of *Mycoplasma hyopneumoniae* for sale. In view of the widespread dissemination of the disease, numerous strains may easily be obtained by recovering *Mycoplasma hyopneumoniae* from lung secretions or tissue from sick animals and inoculating suitable culture medium.

However, *Mycoplasma hyopneumoniae* may rapidly alter its antigens in culture. High passage strains of greater than about 50 passages lose their infectivity and elicit poorer immune protection. Therefore, it is preferable to employ freshly isolated strains or cultured strains which have retained the ability to be infectious in the animal host. While no critical number of generations is known to exist, the present invention preferably starts with a *Mycoplasma hyopneumoniae* strain which has been passed no more than about ten, and preferably only about five or less times before mass scale production. By using strains with fewer generations in culture, it is believed that the antigens retain their natural state and thus will elicit a protective immune response against the infectious microorganism.

In the present invention the large scale production was performed with strains of less than ten passages. Strains of five passages are still infectious. The number of passages where a strain looses infectivity and where it ceases to elicit a protective immune response will vary with the strain but generally occurs somewhere between about 10 and about 50 passages. For the purposes of this application, the term "low-passage" shall mean a strain which remains effective at eliciting an immune response which substantially protects the animal from natural infection.

Recent data suggests that the surface antigen p44 is needed for eliciting protective immunity because protected animals contain high antibody levels to this antigen. Additionally, antibody directed against p44 prevents bacterial growth.

One method to determine whether or not the bacteria is still acceptable for use in a vaccine is to culture the bacteria in the presence of antibody to p44. Should the antibody have no effect on bacterial growth, one can infer that the bacteria lacks or has altered the antigen. This result indicates that the bacteria may not be effective and may be discarded rather than preparing a bacterin vaccine. Alternatively, any of the many standard immunoassay or protein assays may be used to determine whether or not a sample bacteria contains p44.

Should one suspect or find a strain of *Mycoplasma hyopneumoniae* was grown in culture for too long for preparing an effective bacterin, the strain may be freshened by infecting an animal with bacteria and recovering infectious bacteria. This same technique may be employed as an assay to determine whether a cultured strain is sufficiently fresh to provide an effective vaccine. While a strain of *Mycoplasma hyopneumoniae* may remain effective for preparing a vaccine after it loses its infectivity, it is preferable to use infectious or low passage seed stock for large scale production of bacteria for vaccine purposes.

Other species of Mycoplasma including human strains may also be obtained from other investigators, depositories and from the same or different biological sources. Examples of other species of Mycoplasma include, *M. arginini, M. bovis, M. califormicum, M. conjunctivae, M. flocculare, M. gallisepticum, M. hominis, M. hyorhinis, M. hyosynoviae, M. lipofaciens, M. mycoides, M. orale* and *M. pneumoniae.*

Since the *Mycoplasma hyopneumoniae* employed is infectious, one would not wish to give the disease to swine. In the present invention, the bacteria is first inactivated by adding an inactivating amount of Thimerosal (sodium ethyl mercury thiosalicylate or sodium ethyl mercurithio-salicylate) to the bacteria in order to render it non-infectious. The term "Thimerosal" is considered inclusive of its generic equivalents and chemically different compounds which function in the same inactivating manner. For example, another compound providing mercury ions to the bacteria may also be used and be effective.

While applicants do not wish to be bound by any particular theory, one reason why Thimerosal inactivation provides a more protective vaccine may be due to its minimal alteration of the bacterium per se. Certain inactivation methods such as sonication or detergent lysis inactivate the bacteria by disrupting the membranes. Other inactivation methods such as formaldehyde and heat treatment inactivate the bacteria by denaturing proteins. By contrast, Thimerosal is more specific in its action, leaving intact the antigens required to elicit a protective immune response.

One suitable method for Thimerosal inactivation is to add commercially available 10% Thimerosal to a whole bacterial culture or to bacteria separated from *Mycoplasma hyopneumoniae* cultures or infected animal tissues or fluids. The final 25 concentration of Thimerosal needed to completely inactivate *Mycoplasma hyopneumoniae* will vary depending on the concentration of bacteria and the environment of its use. Maintaining about 0.01% Thimerosal for about 24 hours near the growth temperature (about 35° C.) is effective at inactivating the bacteria. This amount is also believed to be lethal as no live *Mycoplasma hyopneumoniae* could be cultured from cultures so treated.

The Thimerosal may be removed from the preparation prior to injecting the vaccine into an animal. However, this amount of Thimerosal is not sufficient to significantly harm the animal receiving a vaccine containing the inactivated bacteria. Therefore, removal of Thimerosal is not required and it may be preferable to leave it to act as a preservative.

The resulting inactivated *Mycoplasma hyopneumoniae,* also called a *Mycoplasma hyopneumoniae* "bacterin", may be employed directly as a vaccine. The effective amount will depend on the species, breed, age, size, health status and whether the animal has previously been given a vaccine against the same organism. The additional components in the vaccine and route of administration will also affect the effective dosage. Each batch of antigen may be individually calibrated. The effective dosage is easily determinable by one of ordinary skill in the art by methodical trials of different dosages.

It is believed that the p44 antigen contributes significantly to the effectiveness of applicants' killed vaccine. Consequently, the monitoring e.g., (immunochemically) of p44 levels in the vaccine preparation may be a useful quality control procedure. Also, one can isolate the p44 antigen alone or with other antigens and use it in the place of the Thimerosal killed bacterin. This antigen may be mixed with other antigens from *Mycoplasma hyopneumoniae* or other microorganisms when using it in a vaccine. P44 may also be self polymerized or chemically coupled to other materials to provide a better immunogen.

Another aspect of producing a protective vaccine involves the use of adjuvants to heighten the immune response sufficiently to substantially prevent natural infection. To enhance immunogenicity of a bacterin or single proteins, adjuvants containing aluminum hydroxide and/or DEAE dextran (diethyl amino ethylether dextran) may be used. The concentration of aluminum hydroxide may be very broad, in the range of up to about 1.5% depending on the route of administration. Concentrations in the range of 0.1 to 1.0% are more typical. Likewise the concentration of DEAE dextran may be wide, e.g., up to about 6% may be used. Most preferred concentrations of aluminum hydroxide and DEAE dextran in the vaccine are from about 0.24% to about 0.39% aluminum hydroxide and about 1.5% of DEAE dextran.

DEAE dextran is commercially available in a variety of molecular weights. While the examples use DEAE dextran with a molecular weight of 500,000 daltons, different sizes may also be used as an adjuvant. Dextran sulfate has been used as an adjuvant but the results were less impressive.

While the preferred bacteria is *Mycoplasma hyopneumoniae,* the combination adjuvant described herein may be used with other bacteria and especially other Mycoplasma. The optimum concentrations of aluminum hydroxide and DEAE dextran may vary from one bacteria to another and from one preparation to another; the optimal concentrations would be readily determined by those using this invention by varying concentrations of each in the presence of fixed concentrations of the other and determining which is most protective.

A change in the concentration of one adjuvant is likely to alter the preferred concentration of the other. The preferred combination of adjuvants would depend on the bacterin used and the animal being vaccinated.

While the present application demonstrates the effectiveness of such an adjuvant with *Mycoplasma hyopneumoniae, Bordetella bronchiseptica* and *Pasteurella multocida* types A and D in particular, it is believed that the mechanism of action is operable for all bacterins from any bacteria. The degree of its enhanced immune response effects may vary with the bacterin but its beneficial effects on bacterial infections remain.

The bacterin, or separated protein(s), whether it is with an adjuvant or not, may be admixed with a acceptable vehicle for vaccination. Well known examples include sterile water, saline, or buffered solutions. Additional agents to improve suspendability and dispersion in solution may also be used. Many conventional vehicles for carrying a vaccine are known and are mentioned in the references above. It is within the abilities of those skilled in the art to select appropriate vehicles depending on the route of administration and condition of the recipient animal.

Immunization may be performed by any conventional route such as oral, intranasal, aerosol and injection (either IM, SC, IV, ID or other method). The route of administration depends on the animal being vaccinated, vaccination history and convenience of the person administering the vaccine. Repeated vaccinations are preferable at periodic time intervals to enhance the immune response initially or after a long period of time since the last dose. The time interval between vaccinations varies depending on the age and condition of the animal. For initial vaccination, the period will generally be longer than a week and preferably will be between about two to three weeks. For previously vaccinated animals, approximately annual, before or during pregnancy inoculations may be performed.

The dosage of vaccine to administer is easily determinable based on the concentration of bacterin, the route of administration and the condition of the animal.

From the examples presented below, it will be readily apparent what approximate dosage would be appropriate. The critical factor is that the dosage provides at least a partial protective effect against natural infection.

*Mycoplasma hyopneumoniae* bacterin may be used alone or in combination with other vaccines for convenience or enhanced results. The combination vaccine preferably provides protection against plural infections. Of particular interest is the combination of *Mycoplasma hyopneumoniae* and *Borderella bronchiseptica* and *Pasteurella multocida* types A and D because all three cause significant disease in swine. Additionally, such combinations do not interfere with each other in their ability to stimulate a protective immune response.

The other vaccines may be inactivated by entirely different means. The other vaccines to be combined with *Mycoplasma hyopneumoniae* bacterin should also be compatible with the same adjuvant used for *Mycoplasma hyopneumoniae* bacterin.

The *Mycoplasma hyopneumoniae* bacterin may also be used as an antigen for diagnostic purposes to determine whether or not a biological test sample contains *Mycoplasma hyopneumoniae* antigens or antibodies to these antigens.

Such an assay for *Mycoplasma hyopneumoniae* infection in an animal typically comprises incubating an antibody containing biological sample from said subject suspected of having such a condition in the presence of a detectably labeled *Mycoplasma hyopneumoniae* bacterin of the present invention, and detecting binding.

Thus, in this aspect of the invention, the *Mycoplasma hyopneumoniae* bacterin may be associated with a solid phase support, e.g., a microtiter plate, which is capable of immobilizing cells, cell particles or soluble proteins. The support may then be washed with suitable buffers followed by treatment with the sample containing antibody. The solid phase support may then be washed with the buffer a second time to remove unbound antibody. Labeled *Mycoplasma hyopneumoniae* is added and the support is washed a third time to remove unbound labeled antigen. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses (especially nitrocellulose), polyacrylamides, agarose, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

Alternatively, the bacterin particle per se may be considered large enough to be its own solid phase. In this situation, the bacterin is mixed with an antibody containing sample and the presence or absence of agglutination is detected.

One of the ways in which the *Mycoplasma hyopneumoniae* specific antibody can be detectably labeled is by linking the same to an enzyme and using it in an enzyme immunoassay (EIA), or enzyme-linked immunosorbent assay (ELISA). This enzyme, in turn, when later exposed to its substrate, will react with the substrate in such a manner as to produce a chemical moiety which can be detected, for example, by spectrophotometric, fluorometric or by visual means. Enzymes which can be used to detectably label the *Mycoplasma hyopneumoniae* specific antibody include, but are not limited to, horseradish peroxidase, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoa/nylase and acetylcholinesterase.

Detection may be accomplished using any of a variety of immunoassays. For example, by radioactively labeling the bacterin, it is possible to detect antibody binding through the use of a radioimmunoassay (RIA). A good description of RIA may be found in *Laboratory Techniques and Biochemistry in Molecular Biology,* by Work, T. S., et al., North Holland Publishing Company, NY, (1978) with particular reference to the chapter entitled "An Introduction to Radioimmune Assay and Related Techniques" by Chard, T., incorporated by reference herein.

The radioactive isotope can be detected by such means as the use of a gamma counter or a scintillation counter or by autoradiography. Isotopes which are particularly useful for the purpose of the present invention are: $^{3}H$, $^{25}I$, $^{131}I$, $^{35}S$, $^{14}C$, and preferably $^{125}I$.

It is also possible to label the bacterin with a fluorescent compound. When the fluorescently labeled bacterin is exposed to light of the proper wave length, its presence can then be detected due to fluorescence. Among the most commonly used fluorescent labelling compounds are fluorescein isothiocyanate, rhodamine, phycoerytherin, phycocyanin, allophycocyanin, o-phthaldehyde and fluorescamine.

The bacterin can also be detectably labeled using fluorescence emitting metals such as $^{152}Eu$, or others of the lanthanide series. These metals can be attached to the bacterin using such metal chelating groups as diethylenetriaminepentaacetic acid (DTPA) or ethylenediaminetetraacetic acid (EDTA).

The bacterin also can be detectably labeled by coupling it to a chemiluminescent compound. The presence of the chemiluminescent-tagged bacterin is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used as a label in the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferass and aequorin.

Detection of the label may be accomplished by a scintillation counter, for example, if the detectable label is a radioactive gamma emitter, or by a fluorometer, for example, if the label is a fluorescent material. In the case of an enzyme label, the detection can be accomplished by colorimetric methods which employ a substrate for the enzyme. Detection may also be accomplished by visual comparison of the extent of enzymatic reaction of a substrate in comparison with similarly prepared standards.

The detection of foci of detectably labeled antibodies is indicative of a disease or dysfunctional state and may be used to measure *Mycoplasma hyopneumoniae* in a sample. For the purposes of the present invention, the bacteria which is detected by this assay may be present in a biological sample. Any sample containing it can be used. However, one of the benefits of the present diagnostic invention is that invasive tissue removal may be avoided. Therefore, preferably, the sample is a biological solution such as, for example, nasal, throat or lung fluid. However, the invention is not limited to assays using only these samples, it being possible for one of ordinary skill in the art to determine suitable conditions which allow the use of other samples.

In situ detection may be accomplished by removing a histological specimen from an animal, and providing the combination of labeled antibodies of the present invention to such a specimen. The antibody (or fragment) is preferably provided by applying or by overlaying the labeled antibody (or fragment) to a biological sample. Through the use of such a procedure, it is possible to determine not only the presence of *Mycoplasma hyopneumoniae* but also the distribution of it in the examined tissue. Using the present invention, those of ordinary skill will readily perceive that any of a wide variety of histological methods (such as staining procedures) can be modified in order to achieve such in situ detection.

Testing a bacteria to determine whether or not it contains p44 may be performed by a conventional growth inhibition assay such as that of Clide, "Growth Inhibition Tests", in *Methods in Mycoplasmology,* vol. 1, Razin et al., eds. (1983) p. 405–410. Suitable antibodies may be generated by immunization of an animal with isolated p44 or purified fractions containing p44 and recovering the serum or by generation of monoclonal antibodies such as that of Wise et al; *Journal of Bacteriology,* 169: p. 5546–5555 (1987). Alternatively any of the above immunoassay formats may be used where the sample contains antigen and the solid phase and/or label contains an antibody capable of binding to p44 directly or indirectly.

Additional description of the invention is presented by way of the following working examples.

EXAMPLE 1:

Preparation of *Mycoplasma hyopneumoniae*

*Mycoplasma hyopneumoniae* strain 11 was obtained from a pig passed lung homogenate obtained from Dr. Richard Ross, Veterinary Medicine Research Institute, Iowa State University, Ames Iowa, and grown in culture for five passages. Typical colonies were chosen each time and growth was shown to be inhibited by monospecific antiserum for *Mycoplasma hyopneumoniae.* The bacteria was used to infect pigs and determined to retain virulence. Infectious bacteria were recovered and cultured for an additional five passages.

Large scale production of bacteria was performed by growing *Mycoplasma hyopneumoniae* at 35°±2° C. for 20 to 100 hours in liquid culture medium with agitation. Growth was monitored by counting cells in an aliquot of medium removed by acridine orange staining and microscopic counting. The culture medium consisted of 30% Hank's Balanced Salt solution, 0.49% Brain Heart Infusion, 0.52% PPLO Broth powder, 0.0025 Mazu antifoam, 4% of 15–20% yeast extract, 10% acid precipitated Swine serum, 10% horse serum and the balance was water with a pH of 7.2±0.2.

EXAMPLE 2

Inactivation of *Mycoplasma hyopneumoniae*

10% Thimerosal solution, no more than six months old, was added to a pH 7.2±0.2 culture at a ratio of 1:1000 to give a final Thimerosal concentration of 1:10,000. The treated culture was incubated for 24 hours at 35°±2° C. with agitation. No viable bacteria were detected after this treatment.

The culture was centrifuged and if needed additional Thimerosal was added to maintain a 0.01% concentration. Potency of the bacterin was determined by measuring p44 protein by western blot assay using monoclonal antibody to p44 such as those of Wise et al., *Journal of Bacteriology,* 169: 5546–5555 (1987). Other monoclonal or polyclonal antibodies specific for p44 may be prepared by immunizing an animal with purified p44 protein and obtaining the desired antibody in a conventional manner.

Units of p44 were determined by scanning the immunoblot and subtracting the background density reading for each immunoblot. The density readings were divided by 100 and entered into the National Veterinary Services Laboratory (NVSn)relative potency program (version 2.0) (Relpot) by the programs' instructions. The relative potency value given for each test serial sample was multiplied by the p44 unit value of the standard to determine the p44 value for the test serial sample.

EXAMPLE 3

Vaccine Production

The vaccine was prepared so that each dose contained at least 50 p44 units. The final concentration of each component per milliliter of vaccine was made to be 70 p44 units, 0.3% aluminum hydroxide, 1.5% DEAE dextran and 0.01% thimerosal in phosphate buffered saline, pH 7.2. The vaccine expiration date is 24 months from the date of a satisfactory potency test.

EXAMPLE 4

Immunization

The vaccine was administered by injection either intramuscularly or subcutaneously. Dosages for young pigs was one ml of vaccine at 5–7 days, one milliliter at 23–28 days. Alternately one milliliter may be given at weaning and one milliliter three weeks later. For pregnant swine, two milliliters were injected at 5 weeks pre farrowing, two weeks pre-farrowing and for subsequent farrowings, one to two weeks pre farrowing. Boars may be treated with a two milliliter dose annually.

Efficacy was demonstrated by vaccination of 110 pigs followed by challenge of those pigs plus 60 control pigs using seven different preparations of the bacteria vaccine described above. No local reactivity was observed at the site of intramuscular injections. Minimal local reactivity was observed at the site of subcutaneous injections. No clinical signs were observed post-vaccination attributable to the vaccination. Weight gains and live birth rates of vaccinated pigs after vaccination were equivalent to those of control pigs. The results are shown in Table 1 below.

EXAMPLE 5

Combination Vaccines

The *Mycoplasma hyopneumoniae* bacterin vaccine described above and other conventional inactivated *Borderella bronchiseptica* and *Pasteurella multocida* types A and D agents were mixed to give the following combinations: A contained all four agents, B contained only the *Mycoplasma hyopneumoniae* bacterin, C contained only *Borderella bronchiseptica* and *Pasteurella multocida* types A and D. These vaccines were administered in accordance with Table 2 and the same protocols were used for the additional Examples. Other sources of *Pasteurella multocida* and *Bordetella bronchiseptica* as well as other bacterial antigens may be used such as those in U.S. Pat. No. 4,559,306.

EXAMPLE 6

Immunization with Combination Vaccines

The potency of the Borderella and Pasteurella type A and D bacterins with and without the *Mycoplasma hyopneumoniae* bacterin was measured in mice following standard procedures and the results are given in Table 3. One can easily see that the addition of *Mycoplasma hyopneumoniae* vaccine was not detrimental to the other vaccine's effectiveness.

Antibody titers were also measured comparing changes in antibody titers of the *Bordetella bronchiseptica* and *Pasteurella multocida* types A and D vaccines both with and without *Mycoplasma hyopneumoniae* bacterin. The results are given in Table 4 where the addition of the *Mycoplasma hyopneumoniae* bacterin appears to enhance antibody titers.

Likewise the effects of *Bordetella bronchiseptica* and *Pasteurella multocida* types A and D vaccines were shown to not only have no negative effects but to enhance the effectiveness of the *Mycoplasma hyopneumoniae* vaccine. The data supporting this is shown in Table 5.

To demonstrate effectiveness at ameliorating the growth retardation effects of *Mycoplasma hyopneumoniae* infection in pigs, the various vaccines were compared to controls and each other with challenge to *Mycoplasma hyopneumoniae*. One can see the statistical significance in the data as given in Table 6.

A comparison between vaccinated and non-vaccinated controls was performed with challenge by two microorganisms. Vaccination was performed with vaccine A given IM at a dosage of 1 ml./pig on days 0 and 21. Two ml./pig of *Mycoplasma hyopneumoniae* was intranasally given on days 35, 36 and 37. *Pasteurella multocida* was administered by intranasal aerosol of one ml./pig and intrapulmonary of 0.2 ml./pig was administered on day 65. Various parameters were compared and the results shown in Table 7.

EXAMPLE 7

Comparison of Effectiveness of Different Passage Numbers

In this example a high passage strain JA of *Mycoplasma hyopneumoniae* which has become calf serum adapted was compared to the relatively fresh strain 11A. The titer of the high passage strain was $3.8 \times 10^9$ CCU/ml whereas the titer of the low passage strain was $3.8 \times 10^8$ CCU/ml. The bacterin was mixed 50/50 with incomplete Freund's adjuvant. The challenge bacteria was at a titer of $10^{7.2}$ CCU/ml. Four pigs eight weeks old were in each group and 2 ml of the bacterins were injected intramuscularly at day zero and 21. The pigs were weighed on days zero, 28 and 56. 2 ml/pig of the challenge bacteria was administered intranasally using an atomizer on days 28, 29 and 30. The animals were killed on day 56 and the pathology analyzed.

All animals were measured for lung lesion scores, clinical signs of morbidity following challenge and the presence of anti-*Mycoplasma hyopneumoniae* antibody titers post-vaccination. Percent protection was calculated as the value of controls minus the value of vaccinates divided by the value of controls multiplied by 100. Low passage *Mycoplasma hyopneumoniae* bacterin gave 82% protection whereas high passage *Mycoplasma hyopneumoniae* gave only 30% protection. Control animals which were not injected with any bacterin gave 0% protection.

EXAMPLE 8

Comparison of Inactivating Agents

The protectiveness of vaccines prepared using three different inactivation agents were evaluated. In each case, 100 ml of *Mycoplasma hyopneumoniae* bulk was inactivated by 1:10,000 Thimerosal, 0.25% formalin or 0.05% beta-propiolactone. Each preparation was centrifuged at 24,000 g for 90 minutes to concentrate the antigen. The pellets were resuspended in 10 ml of fluid to provide a ten-fold concentrate. 1.8 ml of 3% aluminum hydroxide was added to each and two ml of each was injected on days zero and two weeks into each of eight pigs about five weeks of age.

The pigs were challenged 14, 15, 19 and 22 days after the final vaccination. Each pig was administered 6 milliliters intranasally with the standard challenge *Mycoplasma hyopneumoniae* using a nebulizer sprayer. The pigs were sacrificed at four weeks after the initial challenge. Blood was withdrawn from each pig at the time of each vaccination, day of challenge and day of sacrifice. All of the vaccinated pigs seroconverted before challenge whereas the control pigs did not seroconvert until after challenge. The lung lesions were counted on the sacrificed pigs and the data is reported on Table 8.

EXAMPLE 9

Comparison of Different Routes of Administration

Four pigs, eight weeks old, were selected in each group to be inoculated either orally, intranasally or intramuscularly. The protocol of Example 7 was followed using low passage *Mycoplasma hyopneumoniae* bacterin and different groups were inoculated differently for the first inoculation. An adjuvant of 10 mg Avridine, 0.05 ml absolute ethanol, 0.24 ml interlipid, 0.2 ml of 2% aluminum hydroxide and 0.5 ml of interleukin 2 (200 U/ml) per milliliter of bacterin was used. The second dose was given by intramuscular injection. For intranasal vaccination, one milliliter was instilled into each nostril with a blunt needle. Oral administration by mixing the vaccine in milk, thickening it with ground corn and feeding it to the pigs. The degree of protection was measured as in Example 7 above. The intramuscular injected pigs gave 46% protection and both the oral and intranasal administration gave 37% protection.

EXAMPLE 10

Comparison of Different Adjuvants

Following the procedures in Example 7, the low passage *Mycoplasma hyopneumoniae* bacterin was compared by the criteria above between intramuscular injection of incomplete Freund's adjuvant and adjuvant of Example 9. The percentage of protection was 30% with incomplete Freund's adjuvant and 46% with the adjuvant of Example 9.

An additional comparison was made between the intranasally administered adjuvant of Example 9 and two other adjuvants. A first adjuvant contained 10 mg Avridine, 0.15 ml absolute ethanol, 0.85 ml of 10% interlipid, 50 mg TDM/MPL and 0.18 ml 2% aluminum hydroxide per milliliter of bacterin. A second adjuvant contained 0.5 ml of DEAE dextran (400mg/ml) and 0.5 ml of interleukin 2 (200 U/ml) per milliliter of bacterin. The percent protection using the criteria in Example 7 was 37% for the adjuvant of Example 9, 46% for the first adjuvant above and 64% for the second adjuvant above. It should be apparent that the adjuvant containing DEAE dextran (molecular weight about 500,000) is distinctly more effective.

EXAMPLE 11

Adjuvant Effect of Different Dosages of DEAE Dextran and Aluminum Hydroxide

From the data in example 10, the use of aluminum hydroxide was shown to be effective by being a common denominator and the use of DEAE dextran was also shown to be effective. It is therefore assumed that the combination of these two as an adjuvant would be effective. The effectiveness of various concentrations with respect to each other was compared.

Three to four week old pigs were divided into six groups for five different vaccines and were vaccinated with one dose of the bacterin of Example 4 and an adjuvant, twice at a three week interval. An unvaccinated control group F was also used. Seven days after the second vaccination, all pigs were challenged with 2 milliliters of standard pathogenic *Mycoplasma hyopneumoniae* by intranasal aerosol for three consecutive days. Four weeks after challenge, the pigs were sacrificed and the lungs examined for lung lesions. The results are shown in Table 9.

Blood was taken from the pigs at the time of first vaccination and challenge and the serum antibody titers determined by ELISA. Geometric mean titers of anti-*Mycoplasma hyopneumoniae* antibody was measured and the data presented in Table 10.

EXAMPLE 12

Assay for Mycoplasma Growth Inhibition Antibodies Against Mycoplasma Antigens The effects of antibodies to various proteins were tested for the ability to inhibit growth of *Mycoplasma hyopneumoniae* as a measure of whether the protein is a protective antigen. Six plates were used with different antibodies added to each. Monoclonal antibodies were the same as those used by Wise et al, *Journal of Bacteriology*, 169: p. 5546–5555 and were obtained by draining ascites fluid from hybridoma carrying mice. The antibody preparations were ascites fluid anti-p44 *M. hyopneumoniae*, heat treated anti-p44 *M. hyopneumoniae*, anti-p70 *M. hyorhinis*, heat treated anti-p70 *M. hyorhinis*, standard negative anti-*M. hyopneumoniae* serum and standard positive anti-*M. hyopneumoniae* serum. The heat treatment was used to inactivate complement as complement has been known to inhibit growth nonspecifically.

For each plate, the antibody samples were tested undiluted, diluted ½, ¼ and ⅛. 25 μl of each was added to 6 mm Whatman filter paper disc. All four dilutions of each were spaced out evenly on a petri dishes and were incubated overnight. Stock cultures of *Mycoplasma hyopneumoniae* were diluted 1/10 and 0.5 ml of the diluted culture was added to each plate allowed to stand for 30 seconds and then excess fluids poured off before addition of antibody samples. Zones of inhibited growth of *M. hyopneumoniae* greater than 1.5 mm were considered significant. The results are shown in Table 11. The results show that anti-p44 inhibits the growth of *Mycoplasma hyopneumoniae* regardless of complement while all of the inhibitory activity in anti-p70 appears due to complement.

EXAMPLE 13 p44 Vaccine and its Administration

*Mycoplasma hyopneumoniae* p44 is purified from the bacteria by lysis of the bacteria and conventional protein separation and purification procedures known in the art per se. At least about 50 p44 units are used to replace the bacterin given in Example 3 above and are mixed with the adjuvant given in Example 3 above and administered in accordance with the protocol of Example 4 above.

Combination vaccines employing p44 are made by substituting at least about 50 p44 units for the *Mycoplasma hyopneumoniae* bacterin in the combination vaccines provided in Example 6 above.

EXAMPLE 14

Assay of p44 levels in Vaccine Preparations

Vaccine preparations (at any stage in the manufacturing process) may be assayed for p44 levels using the antibody of Wise et al. or equivalent, and compared to the p44 levels in a reference vaccine preparation shown to be protective in pigs.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

TABLE 1

| experimental bacterin | Num. of pigs | Percent Seroconversion | Percent reduction in lung lesions % | % reduction in Mh in lung tissue | ave. weight lb. gain/pig compared to controls |
|---|---|---|---|---|---|
| 1 | 6 | 100 | 74 | 70 | 12.2 |
| 2 | 10 | 100 | 79 | 98 | ND |
| 3 | 6 | 100 | 69 | 84 | 3.0 |
| 4 | 33 | 100 | 80 | 99.5 | 3.2 |
| 5 | 7 | 100 | 70 | 99.9 | ND |
| 6 | 24 | 100 | 62 | ND | 13.8 |
| 7 | 24 | 100 | 63 | ND | 9.2 |

TABLE 1-continued

| experimental bacterin | Num. of pigs | Percent Seroconversion | reduction in lung lesions % | % reduction in Mh in lung tissue | ave. weight lb. gain/pig compared to controls |
|---|---|---|---|---|---|
| total - average | 110 | 100% | 71% | 90% | 8.3 lbs. |

ND = Not determined

TABLE 2

| Group | 1 | 2 | 3 | 4 |
|---|---|---|---|---|
| Bacterin | none | A | B | C |
| Number of gilts | 3 | 6 | 6 | 6 |
| Dose | none | 2 ml. | 2 ml. | 2 ml. |
| Route | none | IM or SC | IM or SC | IM or SC |
| Timing | none | 5 and 2 weeks pre-farrowing | 5 and 2 weeks pre-farrowing | 5 and 2 weeks pre-farrowing |
| Number of pigs* | 26 (12) | 52 (12) | 30 (24) | 41 (23) |
| Dose | none | 1 ml. | 1 ml. | 1 ml. |
| Route | none | IM or SC | IM or SC | IM or SC |
| Timing | none | 5-7 and 23-28 days post-farrowing | 5-7 and 23-28 days post-farrowing | 5-7 and 23-28 days post-farrowing |

*the numbers in parenthesis indicates the number of pigs challenged in a Mycoplasma efficacy test at about 5 weeks of age.

TABLE 3

MOUSE POTENCY RESULTS

| Bacterin | C | A |
|---|---|---|
| Bordetella Survivors Vaccinates | 100% | 100% |
| Bordetella Survivors Controls | 20% | 20% |
| Pasteurella Type A Relative Potency Value | 0.78 | 0.6 |
| Pasteurella Type D - Survivors Vaccinates | 88% | 84% |
| Pasteurella Type D - Survivors Controls | 12% | 12% |

TABLE 4

GEOMETRIC MEAN ANTIBODY TITERS

| Bacterin | No. Gilts | Bordetella Titers Pre-Vaccination | Bordetella Titers Post-Vaccination | Fold |
|---|---|---|---|---|
| C | 4 | 32 | 256 | 8X |
| A | 6 | 20 | 271 | 13X |

| Bacterin | No. Gilts | Pasteurella Titer Pre-Vaccination | Pasteurella Titer Post-Vaccination | Fold |
|---|---|---|---|---|
| C | 4 | 91 | 1,024 | 11X |
| A | 6 | 29 | 1,446 | 50X |

TABLE 5

Mycoplasma hyopneumoniae Antibody Titer Geometric Mean

| Group | 1 & 2 | 3 | 4 |
|---|---|---|---|
| Bacterin | 0 or C | B | A |
| Number of Gilts | 6 | 6 | 6 |
| Gilt Serum Pre-Vaccination | 23 | 25 | 25 |
| Gilt Serum Post-Vaccination | 25 | 287 | 228 |
| Gilt Milk Colostrums | 51 | 676 | 1,626 |
| Gilt Milk 7-day Milk | 3 | 28 | 51 |
| Number of Pigs | 10 | 10 | 11 |
| Pig Serum Pre-Vaccination | 3 | 37 | 32 |
| Pig Serum Post-Vaccination | 2 | 49 | 97 |

TABLE 6

WEIGHT GAIN AND LUNG LESIONS

| Group | 1 | 2 | 3 | 4 |
|---|---|---|---|---|
| Bacterin | None | C | B | A |
| Number of pigs | 12 | 12 | 24 | 23 |
| Average Weight Gain | 8.5 | 14.7 | 17.7 | 22.3 |
| Statistical Significance |  | P < 0.05 | P < 0.05 | P < 0.01 |
| Average Lung Lesion Score | 22.8 | 15.1 | 8.6 | 8.3 |
| Statistical Significance |  | P < 0.1 | P < 0.05 | P < 0.05 |

TABLE 7

DUAL CHALLENGE
*Mycoplasma hyopneumoniae* and *Pasteurella multocida*

| Group | A Vaccinates | Non-Vaccinates |
|---|---|---|
| Number of Pigs | 15 | 10 |
| Average Daily Gain | 0.94 | 0.257 |
| Incidence* | 1/15 (7%) | 8/10 (80%) |
| Morbidity Severity** | 13/450 (3%) | 136/300 (45%) |
| Average Mh Lung Lesion Score | 5.8 | 15.3 |
| Statistical Significance | P < 0.05 |  |
| Average Pm Turbinate Atrophy Score | 1.5 | 4.7 |
| Statistical Significance | P < 0.01 |  |

*Number of pigs with respiratory clinical signs/total pigs
**Number of days showing respiratory clinical signs/total pig days

TABLE 8

Protective Effect of Inactivation Treatments

| Group | Treatment | Lung Lesion Score | Percent Reduced |
|---|---|---|---|
| 1 | Thimerosal | 4.5 | 76% |
| 2 | formalin | 18.25 | 0% |
| 3 | beta-propiolactone | 7.75 | 58% |
| 4 | controls | 18.5 | standard |

TABLE 9

Effect of Differing Adjuvants on Lung Lesions

| Group | % DEAE Dextran | % AL (OH)3 | % reduction in lung lesions compared to control |
|---|---|---|---|
| A | 6 | 0.3 | 79 |
| B | 3 | 0.3 | 89 |
| C | 1.5 | 0.3 | 93 |
| D | 0 | 0.3 | 34 |
| E | 3 | 0 | 70 |

TABLE 10

Effect of Different Adjuvants on Antibody Titers Anti-*Mycoplasma hyopneumoniae* Geometric Mean Titers

| Group | % DEAE Dextran | % Al (OH)3 | Pre-Vac. | Post-Vac. | Fold Increase |
|---|---|---|---|---|---|
| A | 6 | 0.3 | 69 | 294 | 4X |
| B | 3 | 0.3 | 37 | 338 | 9X |
| C | 1.5 | 0.3 | 56 | 446 | 8X |
| D | 0 | 0.3 | 64 | 223 | 3.5X |
| E | 3 | 0 | 74 | 147 | 2X |

Fold Increase = Post-Vac. Titer/Pre-Vac. Titer

TABLE 11

Effects of Antibodies on the Growth of *M. hyopneumoniae*
millimeters of inhibition of surface growth of *M. hyopneumoniae*

| Antibody | Undiluted | ½ | ¼ | ⅛ |
|---|---|---|---|---|
| Anti-p44 *M. hyopneumoniae* | 2.0 | 2.0 | 1.0 | 0.5 |
| Anti-p44 *M. hyopneumoniae* heat inactivated | 2.0 | 3.0 | 1.5 | 1.0 |
| Anti-p70 *M. hyorhinis* | 1.5 | 1.0 | 0.5 | 0 |
| Anti-p70 *M. hyorhinis* heat inactivated | 0 | 0 | 0 | 0 |
| Standard positive antiserum | 2.5 | 2.5 | | |
| Standard negative antiserum | 0 | 0 | | |

What is claimed is:

1. A method for producing a *Mycoplasma hyopneumonia* vaccine comprising contacting live *Mycoplasma hyopneumonia* bacteria with an inactivating concentration of Thimerosal to inactivate the *Mycoplasma hyopneumonia* bacteria, and incorporating the inactivated bacteria into a pharmaceutically acceptable carrier to produce a *Mycoplasma hyopneumonia* vaccine.

2. The *Mycoplasma hyopneumoniae* vaccine produced by the process of claim 1.

3. The method of claim 1, further comprising mixing said inactivated *Mycoplasma hyopneumoniae* bacteria according to claim 1 with an adjuvant comprising aluminum hydroxide and DEAE dextran.

4. The *Mycoplasma hyopneumoniae* vaccine produced by the process of claim 3.

5. The method for preparing a vaccine according to claim 3 wherein sufficient aluminum hydroxide and DEAE dextran are added to yield a field concentration of aluminum hydroxide in the vaccine of about 0.24% to about 0.39% and a final concentration of DEAE dextran of about 1.5%.

6. The *Mycoplasma hyopneumoniae* vaccine produced by the process of claim 5.

7. A method for immunizing swine against an infection by *Mycoplasma hyopneumoniae* comprising administering an effective amount of the vaccine according to claim 2 to swine to elicit a protective immune response therein against infection by Mycoplasma hyopneumoniae.

8. The method according to claim 7 wherein said vaccine is administered by injection.

9. A method for immunizing swine against an infection by *Mycoplasma hyopneumoniae* comprising administering an effective amount of the vaccine according to claim 4, to swine to elicit a protective immune response therein against infection by *Mycoplasma hyopneumoniae*.

10. The method according to claim 9 wherein said vaccine is administered by injection.

11. A method for immunizing swine against an infection by *Mycoplasma hyopneumoniae* comprising administering an effective amount of the vaccine according to claim 6 to swine to elicit a protective immune response against infection by *Mycoplasma hyopneumoniae*.

12. The method according to claim 11 wherein said vaccine is administered by injection.

* * * * *